US008900234B2

(12) United States Patent
Stearns et al.

(10) Patent No.: US 8,900,234 B2
(45) Date of Patent: Dec. 2, 2014

(54) METHOD OF TREATMENT DELIVERY (75) Inventors: Stanley D. Stearns, Houston, TX (US);
H. Max Loy, Jr., Houston, TX (US)

(73) Assignee: Gabriel Institute, Inc., Houston, TX (US)

( * ) Notice: Subject to any disclaimer, the term of this patent is extended or adjusted under 35 U.S.C. 154(b) by 366 days.

(21) Appl. No.: 13/528,418

(22) Filed: Jun. 20, 2012

(65) Prior Publication Data
US 2012/0259340 A1    Oct. 11, 2012

Related U.S. Application Data (60) Division of application No. 12/437,910, filed on May 8, 2009, now Pat. No. 8,251,999, which is a continuation-in-part of application No. 12/064,276, filed as application No. PCT/US2008/054085 on Feb. 15, 2008, now Pat. No. 8,828,001.

(60) Provisional application No. 60/890,831, filed on Feb. 20, 2007, provisional application No. 60/891,183, filed on Feb. 22, 2007.

(51) Int. Cl.
*A61B 17/00* (2006.01)
*A61B 17/16* (2006.01)
*A61B 17/34* (2006.01)

(52) U.S. Cl.
CPC ......... *A61B 17/1642* (2013.01); *A61B 17/3472* (2013.01); *A61B 2017/003* (2013.01)
USPC .......................................................... 606/80

(58) Field of Classification Search
USPC .................. 606/79–85; 600/4, 7, 8
See application file for complete search history.

(56) References Cited

U.S. PATENT DOCUMENTS

| | | | |
|---|---|---|---|
| 550,783 | A | 12/1895 | Elliot et al. |
| 1,630,239 | A | 5/1924 | Binley et al. |
| 2,958,349 | A | 11/1960 | McNutt |
| 2,960,892 | A | 11/1960 | Spravka |
| 3,016,073 | A | 1/1962 | Broussard et al. |
| 3,388,505 | A | 6/1968 | Dreiling |
| 3,618,143 | A | 11/1971 | McKee |
| 4,265,231 | A | 5/1981 | Scheller, Jr. et al. |
| 4,541,423 | A | 9/1985 | Barber |

(Continued)

FOREIGN PATENT DOCUMENTS

WO     2008103606 A2    8/2008
WO     2010129527 A1    11/2010

OTHER PUBLICATIONS

Lee W. Young, International Search Report—PCT/US08/02026, Jun. 11, 2008, 2 pages, United States Patent and Trademark Office as International Search Authority, Alexandria, Virginia, US.

(Continued)

*Primary Examiner* — Nicholas Woodall
(74) *Attorney, Agent, or Firm* — Crain, Caton & James, P.C.; James E. Hudson, III (57) ABSTRACT A minimally invasive method for drilling into bone and for providing for delivery of medical treatment is provided. The method includes use of a drilling system includes a miniature shaft, a bit, a guide tube encapsulating the shaft during drilling and a cortex adapter thereafter to prevent closure of the drilled hole, a stylet to prevent blockage of the resulting passage, and introduction for treatment following removal of the stylet. As a result, a hole, targeted towards a cancerous lesion within the bone, is possible.

5 Claims, 9 Drawing Sheets

(56) References Cited

U.S. PATENT DOCUMENTS

| | | |
|---|---|---|
| 4,941,466 A | 7/1990 | Romano |
| 5,002,546 A | 3/1991 | Romano |
| 5,017,057 A | 5/1991 | Kryger |
| 5,387,218 A | 2/1995 | Meswania |
| 5,395,188 A | 3/1995 | Bailey et al. |
| 5,509,918 A | 4/1996 | Romano |
| 5,569,197 A | 10/1996 | Helmus et al. |
| 5,700,265 A | 12/1997 | Romano |
| 5,709,511 A | 1/1998 | Esmailzadeh |
| 5,772,661 A | 6/1998 | Michelson |
| 5,779,708 A | 7/1998 | Wu |
| 5,928,241 A | 7/1999 | Menut et al. |
| 6,018,094 A | 1/2000 | Fox |
| 6,039,127 A | 3/2000 | Myers |
| 6,257,808 B1 | 7/2001 | Groot |
| 6,309,396 B1 | 10/2001 | Ritland |
| 6,322,565 B1 | 11/2001 | Garner et al. |
| 6,391,017 B2 | 5/2002 | Bays |
| 6,511,266 B1 | 1/2003 | Groot |
| 6,740,090 B1 | 5/2004 | Cragg et al. |
| 6,790,210 B1 | 9/2004 | Cragg et al. |
| 6,818,001 B2 | 11/2004 | Wulfman et al. |
| 7,066,942 B2 | 6/2006 | Treace |
| 7,488,322 B2 | 2/2009 | Brunnett et al. |
| 7,569,056 B2 | 8/2009 | Cragg et al. |
| 7,604,636 B1 | 10/2009 | Walters et al. |
| 2003/0032939 A1 | 2/2003 | Gibbs |
| 2003/0130664 A1 | 7/2003 | Boucher et al. |
| 2003/0220646 A1 | 11/2003 | Thelen et al. |
| 2004/0220577 A1 | 11/2004 | Cragg et al. |
| 2005/0236189 A1 | 10/2005 | Rankin |
| 2005/0267481 A1 | 12/2005 | Carl et al. |
| 2006/0067883 A1 | 3/2006 | Krom et al. |
| 2006/0206131 A1 | 9/2006 | Conquergood et al. |
| 2006/0241630 A1 | 10/2006 | Brunnett et al. |
| 2006/0264896 A1 | 11/2006 | Palmer |
| 2006/0264957 A1 | 11/2006 | Cragg et al. |
| 2007/0055259 A1 | 3/2007 | Norton et al. |
| 2007/0093840 A1 | 4/2007 | Pacelli et al. |
| 2007/0196275 A1 | 8/2007 | Li et al. |
| 2007/0231329 A1 | 10/2007 | Lazar et al. |
| 2008/0154275 A1 | 6/2008 | Assell et al. |
| 2009/0187191 A1 | 7/2009 | Carl et al. |
| 2009/0228014 A1 | 9/2009 | Stearns et al. |
| 2010/0256644 A1 | 10/2010 | Stearns et al. |

OTHER PUBLICATIONS

Lee W. Young, Written Opinion of the ISA—PCT/US08/02026, Jun. 11, 2008, 4 pages, United States Patent and Trademark Office as International Search Authority, Alexandria, Virginia, US.

Lee W. Young, International Preliminary Report on Patentability—PCT/US08/02026, Nov. 8, 2010, 4 pages, United States Patent and Trademark Office as International Search Authority, Alexandria, Virginia, US.

Lee W. Young, Written Opinion of the ISA—PCT/US08/54085, Aug. 7, 2008, 5 pages, United States Patent and Trademark Office as International Search Authority, Alexandria, Virginia, US.

Lee W. Young, International Search Report—PCT/US08/54085, Aug. 7, 2008, 2 pages, United States Patent and Trademark Office as International Search Authority, Alexandria, Virginia, US.

Blaine R. Copenheaver, International Search Report in PCT/US10/33511, Jul. 13, 2010, 2 pages, United States Patent and Trademark Office as International Search Authority, Alexandria, Virginia, US.

Blaine R. Copenheaver, Written Opinion in PCT/US10/33511, Jun. 19, 2010, 4 pages, United States Patent and Trademark Office as International Search Authority, Alexandria, Virginia, US.

Linda Sholl, International Preliminary Report on Patentability in PCT/US10/33511, May 25, 2011, 6 pages, United States Patent and Trademark Office as International Search Authority, Alexandria, Virginia, US.

Nicholas W. Woodall, Requirement for Restriction—U.S. Appl. No. 12/437,910, Jan. 18, 2012, 10 pages, United States Patent and Trademark Office, Alexandria, Virginia, US.

Nicholas W. Woodall, Non-final Rejection—U.S. Appl. No. 12/437,910, Apr. 6, 2012, 6 pages, United States Patent and Trademark Office, Alexandria, Virginia, US.

Michael T. Schaper, Requirement for Restriction/Election—U.S. Appl. No. 12/064,276, Jun. 23, 2011, 7 pages, United States Patent and Trademark Office, Alexandria, Virginia, US.

Michael T. Schaper, Non-Final Rejection—U.S. Appl. No. 12/064,276, Sep. 19, 2011, 9 pages, United States Patent and Trademark Office, Alexandria, Virginia, US.

Michael T. Schaper, Final Rejection—U.S. Appl. No. 12/064,276, Jun. 23, 2011, 8 pages, United States Patent and Trademark Office, Alexandria, Virginia, US.

Nicholas W. Woodall, Notice of Allowance—U.S. Appl. No. 12/437,910, Jun. 11, 20112, 7 pages, United States Patent and Trademark Office, Alexandria, Virginia, US.

Lee W. Young, International Preliminary Report on Patentability—PCT/US08/02026, Nov. 8, 2010, 3 pages, United States Patent and Trademark Office as International Search Authority, Alexandria, Virginia, US.

Nicholas W. Woodall, Notice of Allowance—U.S. Appl. No. 12/437,910, Jun. 11, 2012, 7 pages, United States Patent and Trademark Office, Alexandria, Virginia, US.

Michael T. Schaper, Office Action—U.S. Appl. No. 12/064,276, Apr. 24, 2014, 12 pages, United States Patent and Trademark Office, Alexandria, Virginia, US.

Thomas Dunn, Notification of Transmittal of International Preliminary Report on Patentability—PCT/US08/054085, Aug. 10, 2009, 2 pages, United States Patent and Trademark Office as International Preliminary Examining Authority, Alexandria, Virginia, US.

Thomas Dunn, International Preliminary Report on Patentability—PCT/US08/054085, Aug. 7, 2009, 7 pages, United States Patent and Trademark Office as International Preliminary Examining Authority, Alexandria, Virginia, US.

James E. Hudson III, Response to Non-Final Rejection—U.S. Appl. No. 12/064,276, May 12, 2014, 12 pages, Crain, Caton & James, P.C., Houston, Texas US.

METHOD OF TREATMENT DELIVERY

CROSS REFERENCE TO RELATED APPLICATIONS

This application is a divisional of U.S. Non-Provisional patent application Ser. No. 12/437,910 filed May 8, 2009, U.S. Pat. No. 8,251,999 to which priority is claimed, and which was a continuation in part of U.S. Non-Provisional patent application Ser. No. 12/064,276, Filed Feb. 20, 2008, Now U.S. Pat. No. 8,828,001 which is the national entry of PCT/US08/54085 filed Feb. 15, 2008, which claimed the benefit of U.S. Provisional Patent Application No. 60/890,831 entitled, "Directional Bone Drilling and Methods of Treatment" filed on Feb. 20, 2007 in the United States Patent and Trademark Office and U.S. Provisional Patent Application No. 60/891,183 entitled, "Directional Bone Drilling and Methods of Treatment" filed on Feb. 22, 2007 in the United States Patent and Trademark Office.

STATEMENT REGARDING FEDERALLY SPONSORED RESEARCH OR DEVELOPMENT

Not applicable.

BACKGROUND OF THE INVENTION

1. Field of Invention

The present invention relates to an apparatus to provide delivery of medical treatment to and within tissue or bone. In particular the present invention relates to a minimally invasive and particularly small treatment delivery system including a drill and treatment delivery passage. Additionally, the present invention relates to a minimally invasive and particularly small apparatus for drilling of passages in bone for other purposes, such as the imposition of screws or other devices to fix a bone or bone portion in position.

2. Description of the Related Art

Delivery of medical treatments to tissue, particularly hard tissue and notably the tissue within bone, is particularly difficult. Historically treatment has been delivered through the entire body in sufficient application amounts to ensure the necessary treatment amount reaches the desired tissue. As can be expected, this requires application amounts far in excess of the treatment amount necessary and can result in damage to other parts of the body as well as increased costs. Various solutions have been developed to attempt to reduce the application amount, typically by attempting to isolate the affected area from the body, including shunting of blood flow in the affected limb through a heart/lung machine to allow continued circulation within the limb while isolating the blood flow from the rest of the body. Similarly accessing bone to directly apply any treatment amount or to drill into the bone, such as drilling a passage for screws to fix a bone or bone particle in position, has historically been quite difficult and invasive. Moreover, such passages have generally been no smaller than 0.15875 cm (0.0625 inches). Likewise, drilling such passages has resulted in significant fracturing of the bone itself.

The need therefore exists for apparatus to provide delivery of medical treatment to and within tissue, and notably to tissue within the bone, which permits direct application of only the necessary treatment amount and for a system to access tissue, and particularly tissue within a bone, to directly apply any treatment amount or to drill into the bone such as drilling a passage for screws to fix a bone or bone particle in position, with minimal invasion. A need further exists for an apparatus which may be used with tissue or with bone.

Such a need may be particularly important in the treatment of osteosarcoma and similar cancers of bone.

BRIEF SUMMARY OF THE INVENTION

The present invention overcomes the foregoing drawbacks of previous systems.

The present invention provides an improved system to provide delivery of medical treatment to tissue, which may be within a bone, by providing an improved drill, hypodermic guide tube, a cortex adapter and a stylet. The drilling apparatus includes a miniature shaft, a bit, a hypodermic guide tube and a drive unit. The guide tube may comprise, in part, a hypodermic needle, thus providing a hypodermic guide tube. As a result, precise, straight holes may be drilled, targeted towards a cancerous lesion within the tissue. Once the bit reaches the desired depth, the hypodermic guide tube is retained in place, the bit withdrawn, and a capillary, referred to as a cortex adapter, is inserted through the hypodermic guide tube, through the hole in the bone and into the lesion. A stylet may be inserted in the capillary tube to prevent any movement of bodily fluids up the cortex adapter and to prevent coagulation about the opening of the cortex adapter. When needed, the stylet may be removed and the treatment directed to the tissue though the cortex adapter.

Due to the small diameter of the drill, the hole drilled is particularly small. As can be anticipated a plurality of holes can be drilled, spaced apart to deliver specific quantities of treatment across the lesion.

In another aspect of the present invention, the present invention provides an improved method of delivering medical treatment to and into bone.

The foregoing and other objectives, features, and advantages of the invention will be more readily understood upon consideration of the following detailed description of the invention, taken in conjunction with the accompanying drawings.

BRIEF DESCRIPTION OF THE SEVERAL DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only typical preferred embodiments of the invention and are therefore not to be considered limiting of its scope as the invention may admit to other equally effective embodiments.

In the drawings.

DETAILED DESCRIPTION OF THE INVENTION

The invention may be further understood by the following non-limiting examples. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given. In general the terms and phrases used herein have their art-recognized meaning, which can be found by reference to standard texts, journal references and contexts known to those skilled in the art. The following definitions are provided to clarify their specific use in the context of the invention. All references cited herein are hereby incorporated by reference to the extent not inconsistent with the disclosure herewith.

Figure 1:
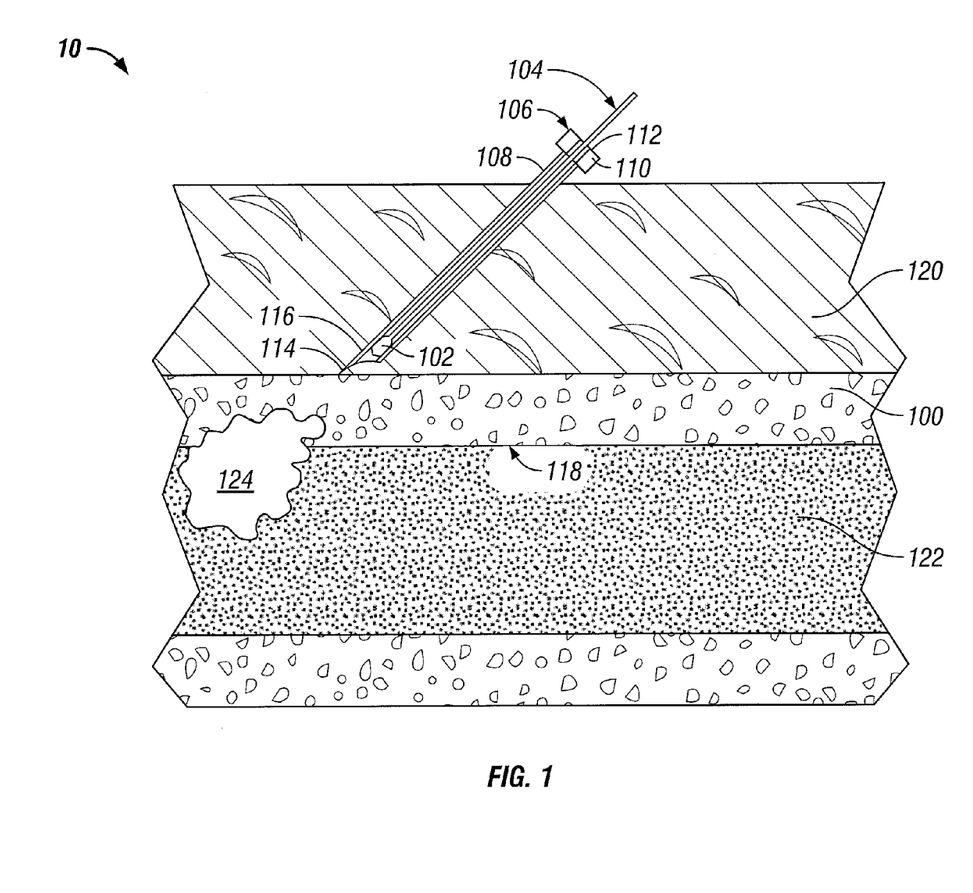
FIG. 1 illustrates a side view of the drilling and hypodermic guide tube portions of the preferred embodiment of the present invention in relation to the bone.
Figure 7:
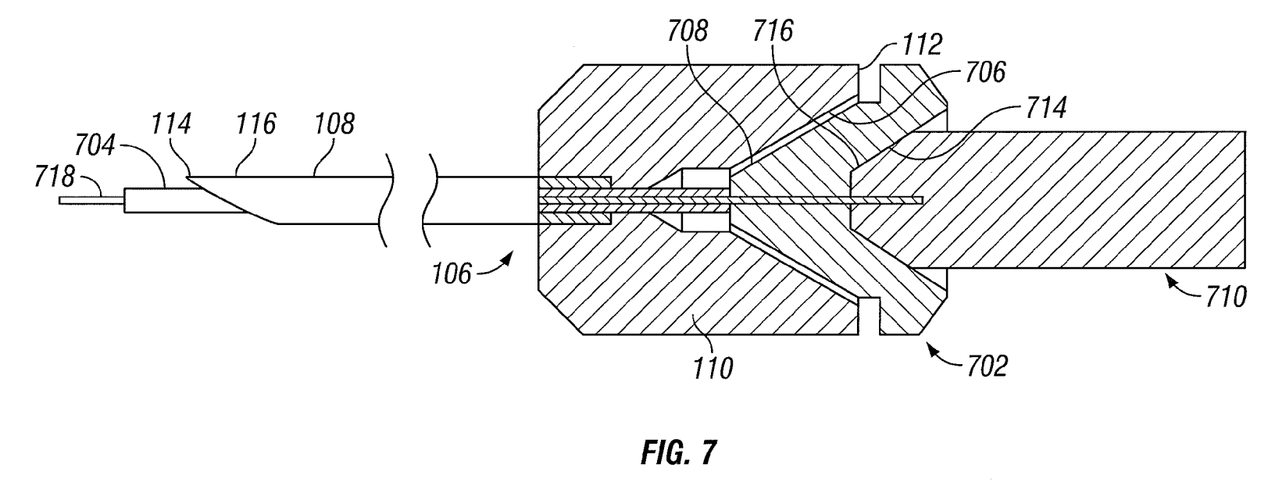
FIG. 7 illustrates a side view of the hypodermic guide tube, cortex adapter and stylet portions of the preferred embodiment of the present invention when nested together.

Referring to the FIG. 1, a portion of a drilling system 10, for drilling into a living bone 100 is shown. The drive unit 1000, depicted in FIG. 10, required for at least partial rotation of the bit 102. The cortex adapter 702 and the stylet 710, depicted in FIG. 7, are not shown. While drilling system 10 is described for use in drilling into bone, it may be used to drill into other body tissues. The drilling apparatus includes a bit 102, a shaft 104, and a hypodermic guide tube 106.

Referring to FIG. 1, the hypodermic guide tube 106 may comprise a hypodermic needle section 108, a hypodermic adapter fitting 110 at the receiving end 112 of the hypodermic guide tube 106, and a sharp non-coring tip 114 at the penetrating end 116 of the hypodermic guide tube 106. The hypodermic guide tube 106 therefore has a passage through its body along its length.

Figure 2:
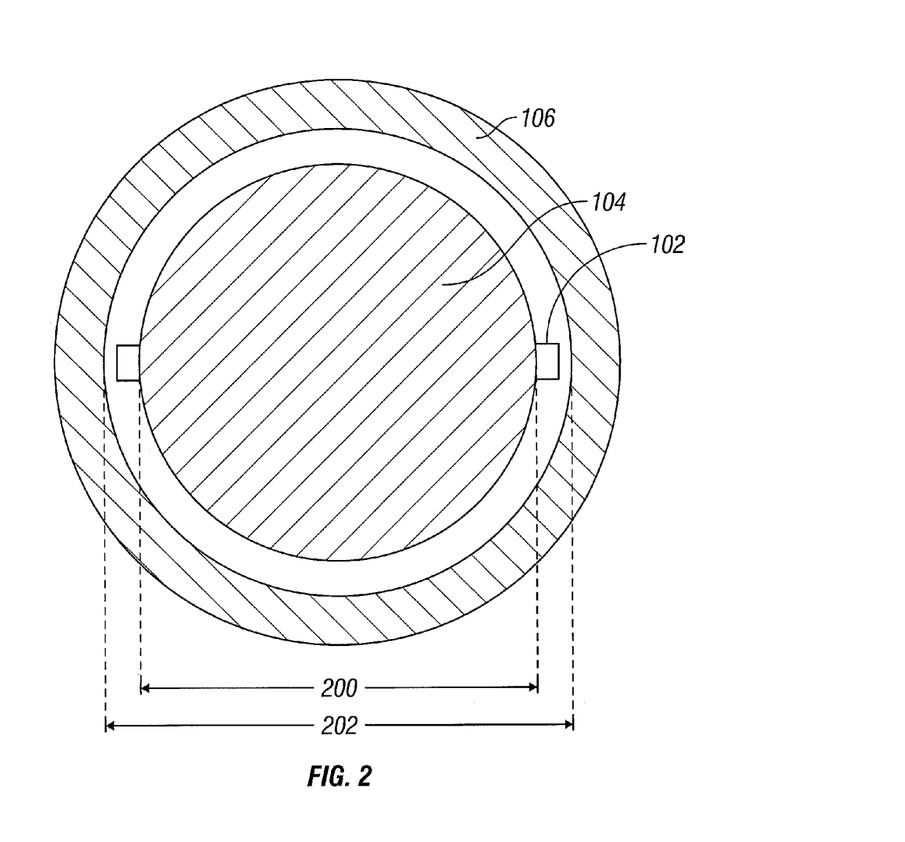
FIG. 2 illustrates a cross sectional view of the drilling and hypodermic guide tube portions of the present invention showing the relation of the shaft and hypodermic guide tube.

Referring to FIG. 2, in the preferred embodiment the hypodermic guide tube 106 is particularly small compared to the bone to be drilled or the body to be entered. The inner diameter 202 of the hypodermic guide tube 106 may be quite small.

Figure 3:
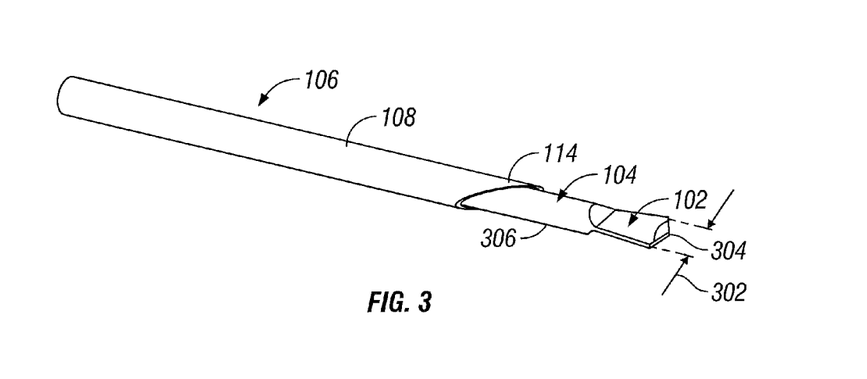
FIG. 3 illustrates a cross-sectional view of the drilling and hypodermic guide tube portions of the present invention, providing a better image of the bit and hypodermic guide tube.

Referring to FIGS. 2 and 3, the shaft 104 and the bit 102 of the drilling system 10 are depicted. A portion of the shaft 104 proximate the first end 306 may be flattened and shaped to produce a bit 102, which may be a spade drill bit. Different bits, such as spherical, helical twist, or burr cutting tips, may alternatively be used. Unlike standard drill bits, which have high strength and brittleness, the bit 102 is quite ductile. As can be appreciated, the loss of such a drill bit in the body, made more likely with a brittle drill bit, is to be avoided. The bit 102 has a width 302 smaller than the inner diameter 202 of the hypodermic guide tube 106, such that the hypodermic guide tube 106 limits the flexing of the shaft 104 but permits withdrawal of the shaft 104 with the bit 102 after use. The bit 102 also has a drill point or cutting edge 304. The shaft 104 therefore has a quite small outer diameter 200. The hypodermic guide tube 106 is therefore sized to surround the shaft 104.

Figure 4:
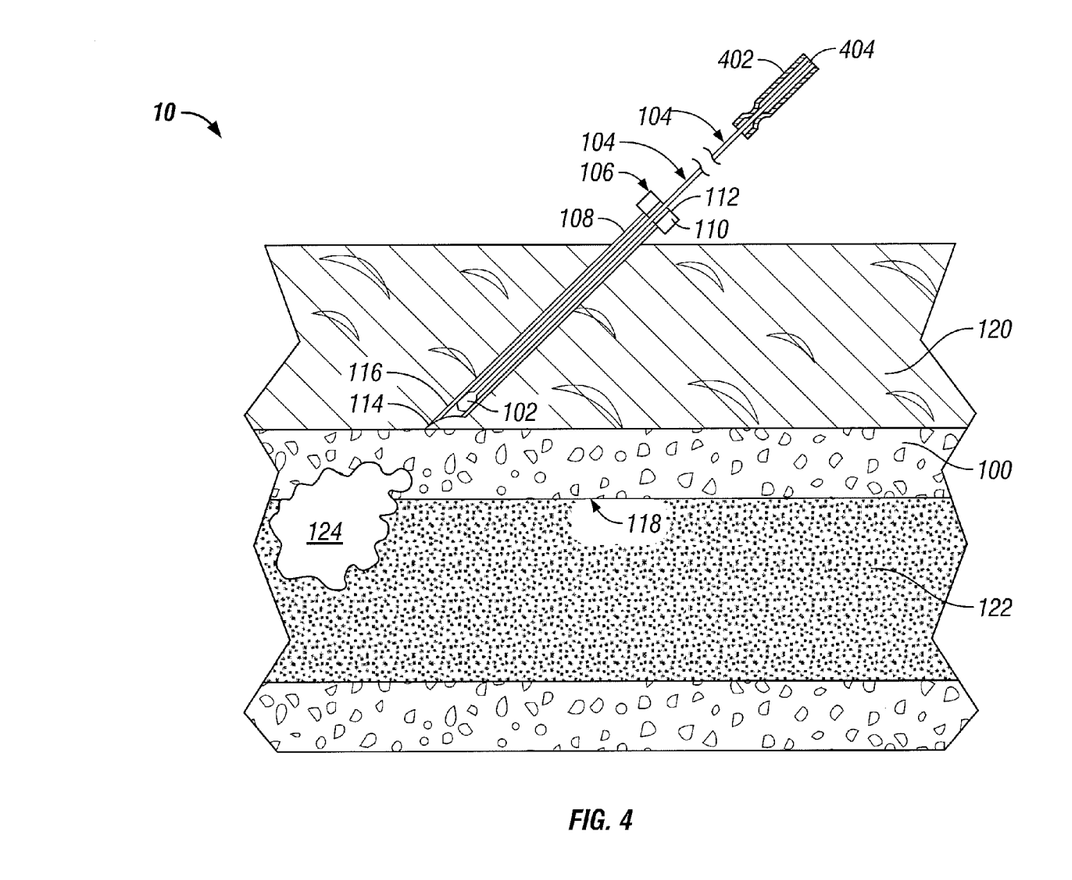
FIG. 4 illustrates a side view of the drilling and hypodermic guide tube portions of the preferred embodiment of the present invention in relation to the bone in relation to a drive tube connected to the drill shaft.

Referring to FIG. 4, a drive tube 402, having a larger diameter than the shaft 104, may enclose the shaft 104 at its shaft second end 404 so the shaft 104 may be connected to a motor or other radial driver to at least partially rotate the shaft 104 and to a linear driver to drive the bit 102 into the bone 100 in operation. The drive tube 402, affixed or connected to the shaft 104, provides for better application of rotational and linear force due to its larger size, but the shaft 104 may be drive without a drive tube 402.

Figure 5:
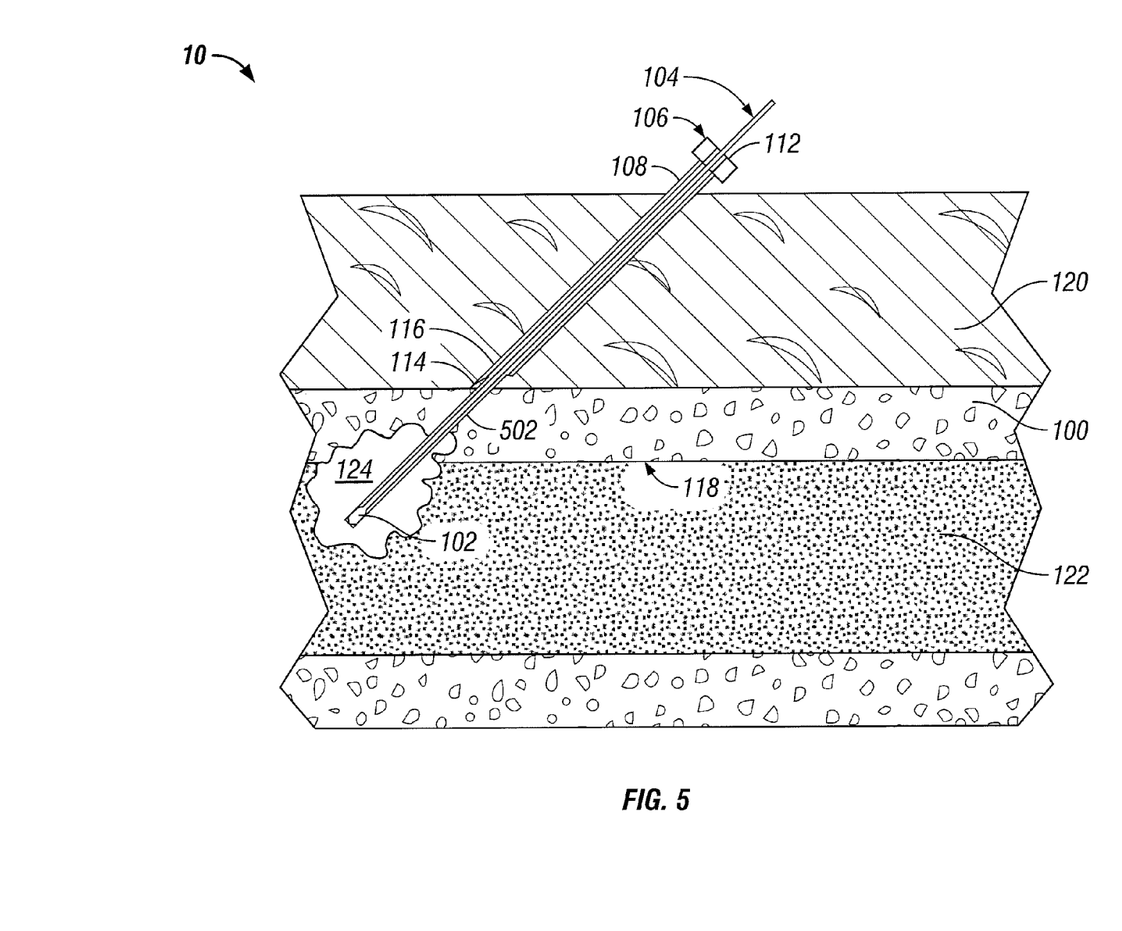
FIG. 5 illustrates a side view of the drilling and hypodermic guide tube portions of the preferred embodiment of the present invention in relation to the bone after penetration through the bone and into a cancerous lesion.

Referring again to FIG. 1 and to FIG. 5, the shaft 104 has a length sufficient to fully pass through the hypodermic guide tube 106 and to drill through the wall 118 of the bone 100.

In operation, the hypodermic guide tube 106 is placed in abutment or proximate to the tissue, here bone 100, at its penetrating end 116. The drilling system 10 may be delivered directly to the bone or tissue to be drilled by driving the hypodermic guide tube 106 through tissue. Alternatively, the drilling system 10 may be placed adjacent or proximate the bone 100 after site preparation, which may include surgical relocation of intermediate parts of the body 120, such as muscle and blood vessels.

Referring to FIGS. 1, 3, and 5, the hypodermic guide tube 106 may include a sharp non-coring tip 114 extending from the hypodermic guide tube penetrating end 116. The length of the sharp non-coring tip 114 is sufficient to maintain a desired angle of drilling while the penetrating end 116 contacts the bone 100 and prevents the cutting tip 304 from contacting the bone 100 prior to advancing the cutting bit 102. The sharp non-coring tip 114 is sized to ensure contact between the hypodermic guide tube 106 and the bone 100 before the cutting bit 102 begins cutting into the bone 100 at the desired angle of attack. Referring to FIG. 1, by virtue of the sharp non-coring tip 114, the hypodermic guide tube 106 contacts the bone 100, or tissue on the surface of the bone 100, and becomes stationary, thereby preventing the cutting bit 102 from walking away from the point of its initial contact with the bone 100 or tissue on the surface of the bone 100. Moreover, as the sharp non-coring tip 114 provides a limited point of contact between the bone 100 and the hypodermic guide tube 106, any chips of bone 100 created by the cutting bit 102 are not trapped adjacent to the cutting bit 102 but rather may escape the passage 502, depicted in FIG. 5, created by the cutting bit 102.

Referring to FIG. 5, the shaft 104 is then driven so that the bit 102 is rotated against the bone 100, while the shaft 104 is advanced, cutting through the bone wall 118, until reaching the marrow 122 and creating a passage 502.

Figure 6:
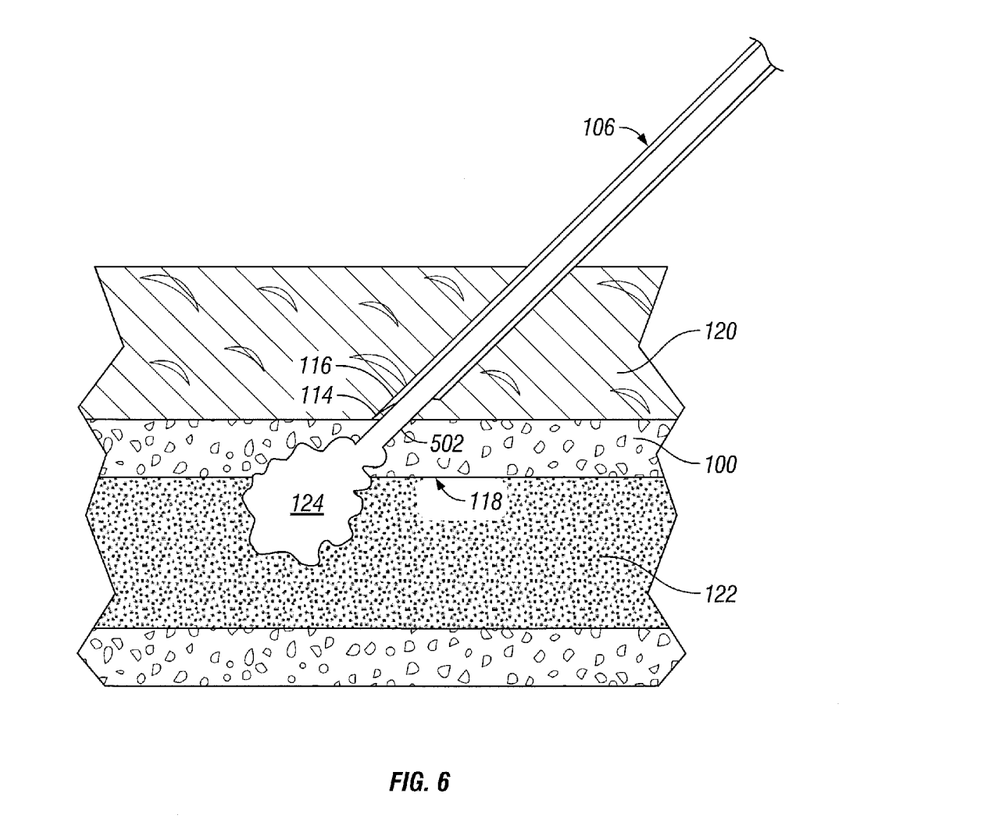
FIG. 6 illustrates a side view of the hypodermic guide tube portion of the preferred embodiment of the present invention in relation to the bone after removal of the drill portion after penetration through the bone and into a cancerous lesion, leaving a usable passage to the cancerous lesion.

Referring to FIG. 6, the bit 102, and the shaft 104 are then withdrawn from the hypodermic guide tube 106, leaving only the hypodermic guide tube 106 in contact with the bone 100 and in communication with the passage 502. The sharp non-coring tip 114 is therefore of critical importance in maintaining the position of the hypodermic guide tube 106 relative to the passage 502 and to providing the means to identify the location of the passage 502.

Figure 8:
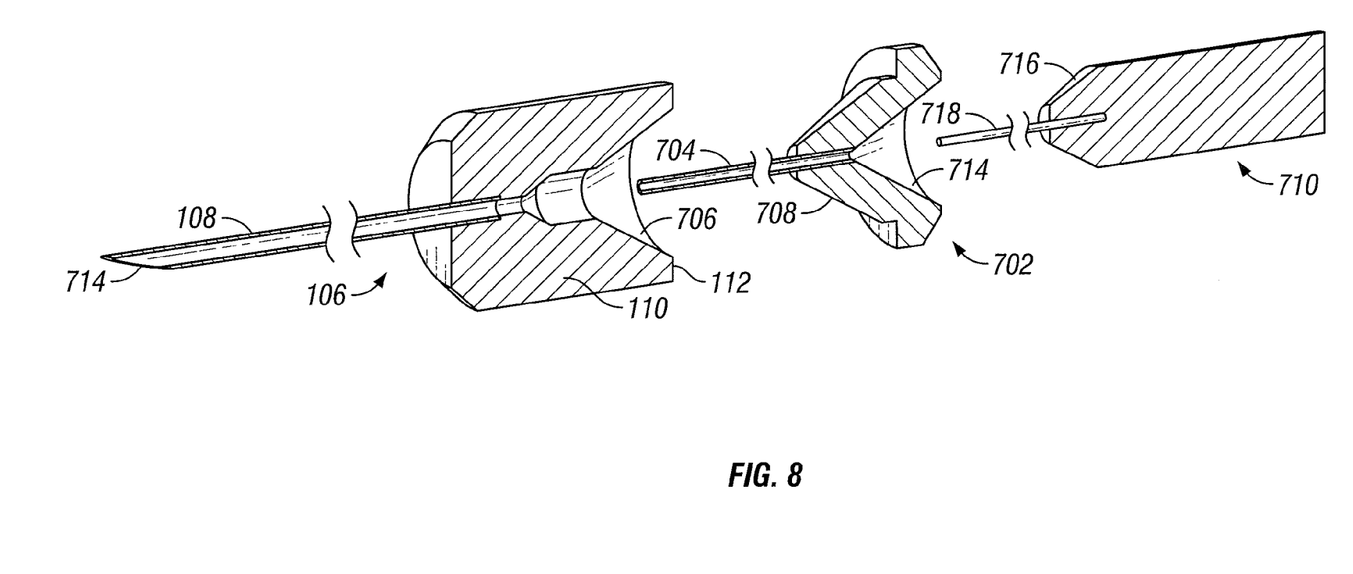
FIG. 8 illustrates a side view of the hypodermic guide tube, cortex adapter and stylet portions of the preferred embodiment of the present invention separated for clarity.
Figure 9:
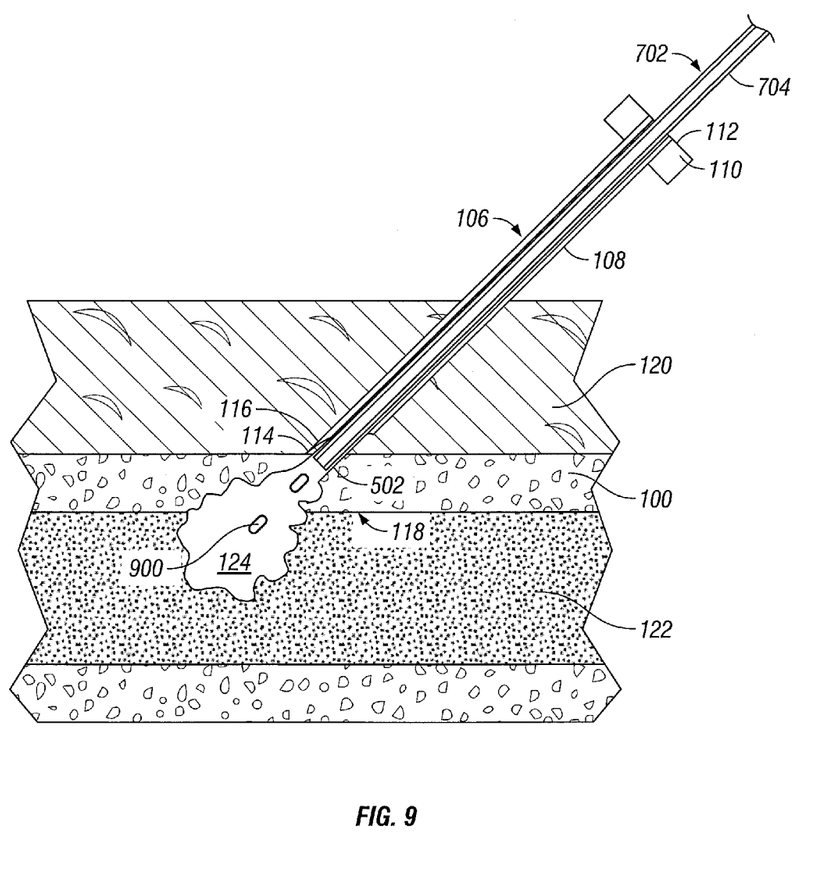
FIG. 9 illustrates a side view of the hypodermic guide tube portion and cortex adapter portions of the preferred embodiment of the present invention in relation to the bone after penetration through the bone and into a cancerous lesion during delivery of a treatment.

Referring to FIGS. 7 and 8, a cortex adapter 702 having a capillary 704 with an interior passage is provided for insertion into the passage of guide tube 106 and ultimately into the tissue passage 502, which may be into the marrow 122, permitting delivery of the treatment 900 as shown in FIG. 9. The hypodermic adapter fitting 110 of the hypodermic guide tube 106 may include a tapered conic cavity 706 adapted to direct the bit 102 and the drill shaft 104 into the hypodermic needle section 108 via hypodermic adapter fitting 110 of the hypodermic guide tube 106. The cortex adapter 702 may be constructed to include a nose 708 to fit into the tapered conic cavity 706 of the hypodermic guide tube 106 and may similarly include a tapered conic cavity 714 adapted to direct the stylet 710 into the hypodermic needle section 108 of the hypodermic guide tube 106. Referring to FIG. 9, the capillary 704 of the cortex adapter 702 is sized and capable of passing through the passage of the hypodermic guide tube 106 and extends the length of the hypodermic guide tube 106, through the passage 502 and through the bone 100 and the marrow 122 to provide a controlled passage of any treatment 900. Referring now to FIGS. 8 and 9, as previously mentioned, the drilling system 10 also includes a stylet 710, which is utilized to plug the cortex adapter 702 when the cortex adapter 702 is not in use, to prevent outflow through the cortex adapter 702, and to prevent coagulation of blood in or at the end of passage 502. To accomplish these goals, the wire section 718 of stylet 710 is capable of fitting within and through the cortex adapter 702 and may preferably extend the entire length of the capillary 704 and into the marrow 122, as depicted in FIG. 7. The stylet 710 may be constructed to include a nose 716 to fit into the tapered conic cavity 714 of the cortex adapter 702. The wire section 718 of the stylet 710 is sized to fit within the cortex adapter 702 sufficiently close to preclude outflow of bodily fluids through the cortex adapter 702, but not so close as to be irremovable from the cortex adapter 702. Ideally both the cortex adapter 702 and the wire section 718 of the stylet 710 have cylindrical cross-sections to encourage this close fit.

Referring to FIG. 8, an exploded view of the constituent parts, including the hypodermic guide tube 106, the cortex adapter 702, and the stylet 710 are depicted.

Referring to FIG. 9, when sufficient numbers of cortex adapters 708 have been inserted into the tissue, the treatment 900 may be introduced into the cancerous lesion 124 through the cortex adapter 702.

The bone 100 is relatively soft when drilled in this manner, thus the drilling system 10 is capable of drilling through the bone 100 without deleterious effects on the surrounding bone. Moreover, the drilling system 10 produces a uniform, clean and particularly small diameter passage 502 through the bone 100. As a result of the small passage 502 directed toward the cancerous lesion 124, any of the various treatments known in the art, such as chemotherapy, radiochemical therapy, directed energy, may be provided without damage of adjacent tissue.

Figure 10:
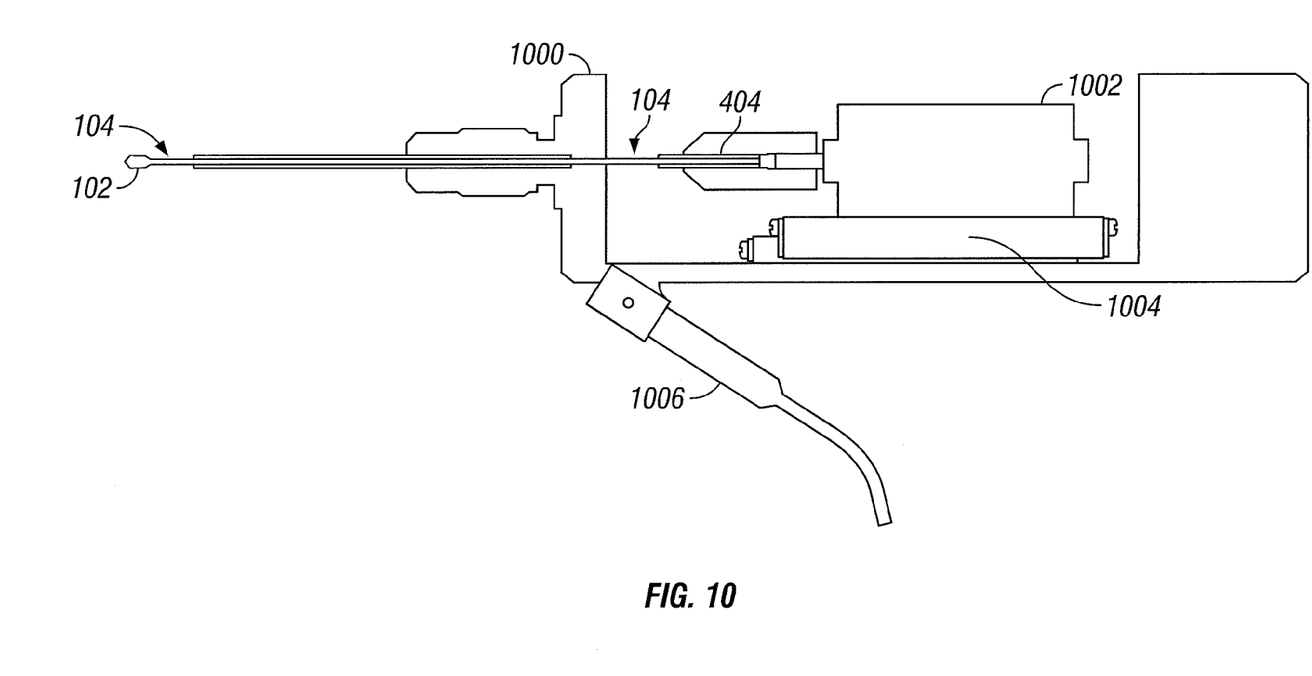
FIG. 10 illustrates one embodiment of the drive unit used with the drilling system.

Referring to FIG. 10, the drilling system 10 may be driven by a drill unit 1000. The drive unit 1000 may include a rotating motor 1002 capable of operable connection to the shaft 104 and capable of at least partially rotating the shaft 104. In the preferred embodiment, the rotating motor 1002 is a rotating motor. The rotating motor 1002 may operate at a fixed speed and is ideally activated when the control arm 1006 is engaged, although a variable speed rotating motor 1002 may be used and as the rotating motor 1002 may be activated by other switches, such as a simple switch or a foot pedal. Regardless of the type of activation used or the fixed or variable speed, the operating speed of the rotating motor 1002 is sufficiently high to efficiently cut the bone 100 without fracturing the bone and low enough to prevent generating thermal necrosis. A control arm 1006 associated with the drive unit 1000 may be moved through a range of positions, causing a linear drive 1004 to advance. The advance of the linear drive 1004 may be proportional to the movement of control arm 1006, particularly if the control arm 1006 is moved radially, thus providing a moment about a pivot to provide a linear drive 1004. The proportion of movement may be set to provide a leverage advantage in linearly driving the shaft 104. The control arm 1006 may also be spring-loaded to cause the linear drive 1004 to retreat as the control arm 1006 is released. Alternatively, the control arm 1006 may be connected to a processor or other system to proportionally multiply the movement of the control arm 1006 to the input of a linear drive 1004. The linear drive 1004 may be coupled or otherwise related to the shaft 104, which may be via a connection of the linear drive 1004 to the rotating motor 1002. Thus as the linear drive 1004 advances and retreats by operation of the control arm 1006, the shaft 104 likewise advances or retreats.

In either embodiment, the bit 102 drills through the bone 100 to provide for application of the medical treatment 900, as illustrated in FIG. 9. Once a passage 502 has been drilled through the bone 100, the medical treatment 900 may be introduced toward the cancerous lesion 124. The treatment 900 may be chemotherapy, radiotherapy, heat therapy or any other therapy known in the art. The amount of treatment 900 necessary for effective treatment may be far less than typically applied when given orally or introduced into the blood stream since the treatment 900 is introduced proximate the cancerous lesion 124. Likewise, the treatment 900 may be more effective as a result of directed application. As can be appreciated, the flow of the treatment 900 through the cortex adapter 702 toward the cancerous lesion 124 is limited by the uptake by the cancerous lesion 124 of the treatment 900.

Alternatively, the treatment 900 may be directed toward the cancerous lesion 124 by a charge-driven application (not shown). Thus it may be possible to enhance the flow of the treatment 900 by applying a direct current potential between the cortex adapter 702 and an electrode in conductive contact with the exterior of the limb placed as closely as possible to the region of the cortex adapter 702. In one embodiment, a very fine liquid aerosol is generated and applied through electrostatic charging. In one embodiment, a liquid is passed through a nozzle, wherein a plume of droplets is generated by electrically charging the liquid to a very high voltage. The charged liquid in the nozzle becomes unstable as it is forced to hold more and more charge. Soon the liquid reaches a critical point, at which it can hold no more electrical charge and at the tip of the nozzle it blows apart into a cloud of tiny, highly charged droplets. These tiny droplets are particularly small, and fly about searching for a potential surface to land on that is opposite in charge to their own. Such droplets would be attracted to the cancerous lesion due to electrical differential. The system may employ a sharply pointed hollow metal tube, such as a syringe needle, with liquid pumped through the tube. A high-voltage power supply may then be connected to the outlet of the tube and the tube positioned proximate a cancerous lesion 124. When the power supply is turned on and adjusted for the proper voltage, the liquid being pumped through the tube transforms into a fine continuous mist of droplets that fly rapidly toward the cancerous lesion 124.

Alternatively, if the treatment 900 consists of direct energy to be applied to the cancerous lesion 124, an optical tube sheathed in a metal, such as nickel, may be used to direct the treatment 900.

Additionally, via the passage 502, it is possible to visually observe the cancerous lesion 124, such as with appropriately-sized fiber-optic or laparoscopic devices.

Thus in operation, the drilling system 10 is applied to or in close proximity to the bone 100 at the penetrating end 112 of the hypodermic guide tube 106. The shaft 104 and the bit 102 are rotated sufficient to cut the bone 100. Force is linearly applied to the shaft 104, which drives the bit 102 into the bone 100 and through the bone wall 118 to create a passage 502. Additionally, it is possible to direct the hypodermic guide tube 106 against the bone 100 towards the cancerous lesion 124 from the opposite side of the cancerous lesion 124. The shaft 104 and bit 102 are removed from the hypodermic adapter fitting 110 of the hypodermic guide tube 106 and the cortex adapter 702 and its capillary 704, together with a stylet 710 therein, are inserted into the hypodermic adapter fitting 110 of the hypodermic guide tube 106. While the cortex adapter 702 may alternatively be first inserted into the hypodermic guide tube 106 and the stylet 710 inserted thereafter, this is not the most desired operation as it permits backflow of bodily fluids into the cortex adapter 702. When the treatement 900, which may be radioactive, is ready to introduction, the stylet 710 is removed and the treatment introduced. Thereafter the hypodermic guide tube 106 and the cortex adapter 702 are removed, thus leaving treatment 900 at the desired location.

The terms and expressions which have been employed in the foregoing specification are used therein as terms of description and not of limitation, and there is no intention, in the use of such terms and expressions, of excluding equivalents of the features shown and described or portions thereof.

We claim:

1. A method for drilling into living bone comprising:
   providing a drill, said drill having a shaft, a cutting bit, a guide tube, and a drive unit,
      said shaft having a first end,
      said cutting bit located at said shaft first end, said cutting bit being ductile, and
      said cutting bit having width,
      said guide tube surrounding said shaft, said guide tube having a sharp non-coring tip at its end, said guide tube having an interior passage, and said guide tube having length,
      said drive unit operably connected to said shaft,
   applying said guide tube to the surface of said bone,
   at least partially rotating said shaft by operation of said drive unit;
   cutting said bone by said cutting bit;
   advancing said shaft and said bit into said bone;
   removing said drill from said guide tube;
   providing a cortex adapter,
      said cortex adapter having a first end, said cortex adapter sized to pass through said interior passage of said guide tube, said cortex adapter having length greater than said length of said guide tube, and said cortex adapter having an interior passage, said cortex adapter having an outer diameter at said first end of said cortex adapter, said outer diameter of said cortex adapter at said first end of said cortex adapter equivalent to but not greater than said width of said cutting bit;
   inserting said cortex adapter into said guide tube and into said tissue at said first end of said cortex adapter,
   providing a stylet,
      said stylet having length sufficient to pass through said cortex adapter;
   inserting said stylet into said cortex adapter;
   removing said stylet from said cortex adapter; and
   introducing a treatment to said living bone through said cortex adapter.

2. The method of claim 1 wherein said drive unit linearly advances said shaft.

3. The method of claim 1 wherein said tissue is bone.

4. The method of claim 3 wherein said stylet has a length greater than said length of said cortex adapter.

5. The method of claim 1 wherein said cutting bit is formed at said first end of said shaft.

\* \* \* \* \*